US006289233B1

(12) United States Patent
Dumoulin et al.

(10) Patent No.: US 6,289,233 B1
(45) Date of Patent: Sep. 11, 2001

(54) HIGH SPEED TRACKING OF INTERVENTIONAL DEVICES USING AN MRI SYSTEM

(75) Inventors: Charles Lucian Dumoulin, London (GB); Robert David Darrow, Scotia, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/199,405

(22) Filed: Nov. 25, 1998

(51) Int. Cl.[7] .................................................. A61B 5/055
(52) U.S. Cl. ............................................. 600/410; 324/309
(58) Field of Search ...................................... 600/410, 424, 600/423; 324/307, 309

(56) References Cited

U.S. PATENT DOCUMENTS

| | | |
|---|---|---|
| 4,830,012 | 5/1989 | Riederer ................................ 128/653 |
| 5,211,165 | 5/1993 | Dumoulin et al. . |
| 5,271,400 | 12/1993 | Dumoulin et al. . |
| 5,307,808 | 5/1994 | Dumoulin et al. . |
| 5,318,025 | 6/1994 | Dumoulin et al. . |
| 5,353,795 | 10/1994 | Souza et al. . |
| 5,617,857 | 4/1997 | Chader et al. . |
| 5,622,170 | 4/1997 | Schulz . |
| 5,715,822 | 2/1998 | Watkins et al. . |
| 5,810,728 | * 9/1998 | Kuhn ..................................... 600/410 |
| 5,882,304 | * 3/1999 | Ehnholm et al. ..................... 600/411 |
| 5,947,900 | * 9/1999 | Derbyshire et al. . |
| 5,951,472 | * 9/1999 | Van Vaals et al. ................... 600/411 |

\* cited by examiner

*Primary Examiner*—Marvin M. Lateef
*Assistant Examiner*—Shawna J Shaw
(74) *Attorney, Agent, or Firm*—Jean K. Testa; Donald S. Ingraham

(57) ABSTRACT

An MRI system acquires NMR tracking data from a tracking coil imbedded in a medical device which is guided by a physician using real time anatomic images produced from image data acquired by the MRI system. A Hadamard magnetic resonance tracking sequence is used to update the tracking coil location which is indicated on the anatomic image. The Hadamard sequence uses four different acquisition, but tracking coil location is updated after each acquisition, using the new acquisition and three previously acquired acquisitions.

13 Claims, 3 Drawing Sheets

HIGH SPEED TRACKING OF INTERVENTIONAL DEVICES USING AN MRI SYSTEM

BACKGROUND OF THE INVENTION

The field of the invention is nuclear magnetic resonance imaging (MRI) methods and systems. More particularly, the invention relates to the tracking of interventional devices using MRI methods.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles, or "views", in which these gradients vary according to the particular localization method being used. The resulting set of received NMR signals are digitized and processed to reconstruct the image using one of many well known reconstruction techniques.

Intra-operative MR imaging is employed during a medical procedure to assist the doctor in guiding an instrument. For example, during a needle biopsy the MRI system is operated in a real-time mode in which image frames are produced at a high rate so that the doctor can monitor the location of the needle as it is inserted. A locator device such as that described in U.S. Pat. No. 5,622,170 and 5,617,857 may be used to track the location of the instrument and provide coordinate values to the MRI system which enable it to mark the location of the instrument in each reconstructed image. The medical instrument is attached to a handpiece that is manipulated by the physician and whose position is detected by surrounding sensors. For example, the handpiece may emit light from two or more light emitting diodes which is sensed by three stationary cameras.

Tracking devices which employ the MRI system to locate markers in the medical device have also been developed. As described in U.S. Pat. Nos. 5,271,400; 5,307,808; 5,318,025; 5,353,795 and 5,715,822, such tracking systems employ a small coil attached to a catheter or other medical device to be tracked. An MR pulse sequence is performed using the tracking coil to produce transverse magnetization at the location of the tracked device. The location of the tracking coil is determined and is superimposed at the corresponding location in a medical image acquired with the same MRI system.

To accurately locate the tracking coil, position information is obtained in three orthogonal directions that require at least three separate measurement pulse sequences. To correct for errors arising from resonance offset conditions, such as transmitter misadjustment and susceptibility effects, two measurements may be made in each direction with the polarity of the readout gradient reversed in one measurement. This tracking method requires that six separate measurement pulse sequences be performed to acquire the tracking coil location. As disclosed in U.S. Pat. No. 5,353,795, these separate measurements can be reduced to four in number by altering the readout gradients in a Hadamard magnetic resonance tracking sequence.

During a medical procedure in which the location of the tracking coil is periodically acquired and used to update a display, the tracking coil measurement acquisitions are interleaved with image data acquisitions. The rate at which the MR image is updated and the rate at which the medical device position is updated on the image are important system requirements. If the tracking coil position is updated is too slowly, the device will not move smoothly on the display but will instead, jump from one position to the next. Since it requires from three to six separate measurements to update the tracking coil position as described above, the rate at which this update can be performed is limited.

SUMMARY OF THE INVENTION

The present invention is a method for tracking a medical device with an MRI system employed to guide a medical procedure. More specifically, a coil is disposed in the medical device to be tracked and the MRI system performs a plurality of different coil tracking measurements in which the tracking coil is employed to acquire NMR tracking data from which the location of the tracking coil in the MRI system is determined, repeatedly performing the plurality of different coil tracking measurements to update the acquired NMR tracking data; and calculating a new tracking coil location after each tracking coil measurement.

The present invention enables the tracking coil location to be updated at a higher rate without increasing the number of coil tracking measurements. Rather than waiting for an entirely new set of NMR tracking data to be acquired, the coil location is determined after each coil tracking measurement. If the above described Hadamard MR tracking sequence is used, for example, the coil location is updated at a rate four times as fast as prior methods.

DESCRIPTION OF THE PREFERRED EMBODIMENT

Figure 1:
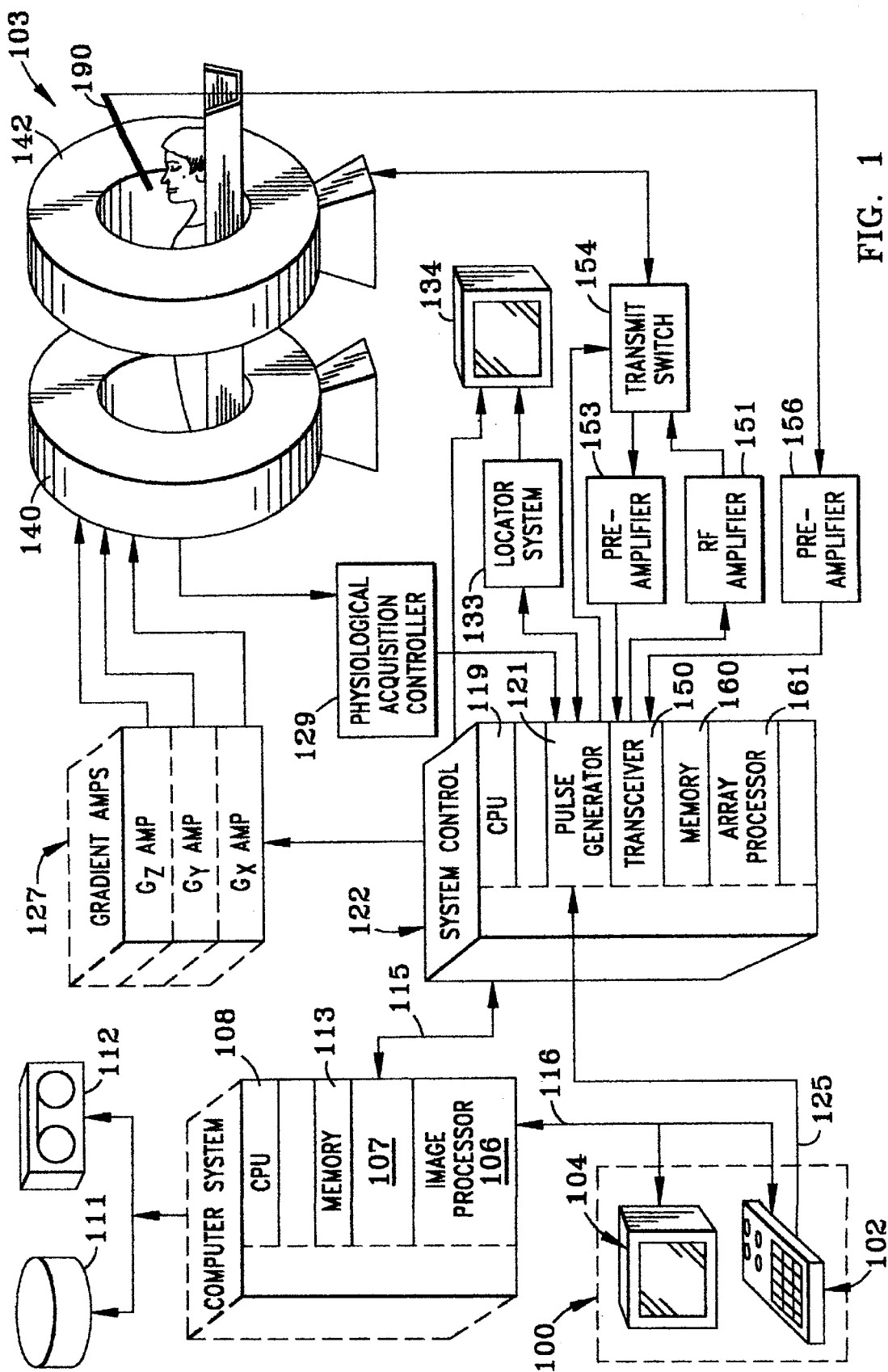
FIG. 1 is a block diagram of an MRI system which employs the present invention.

Referring first to FIG. 1, there are shown the major components of a preferred MRI system which incorporates the present invention. The operation of the system is controlled from an operator console 100 which includes a keyboard and control panel 102 and a display 104. A separate display (not shown) is also located near the magnet system 103 so that they are available to a physician attending the subject of an MRI scan. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a locator system 133.

The gradient waveforms produced by the pulse generator module 121 are applied to a gradient amplifier system 127 comprised of $G_x$, $G_y$ and $G_z$, amplifiers. Each gradient amplifier excites a corresponding gradient coil in the magnet system 103 to produce the magnetic field gradients used for position encoding acquired signals. A transceiver module 150 in the system control 122 produces pulses which are amplified by an RF amplifier 151 and coupled to an RF coil in the magnet assembly 103 by a transmit/receive switch 154. The resulting signals radiated by the excited nuclei in the patient may be sensed by the same RF coil and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the RF coil during the transmit mode and to connect the preamplifier 153 during the receive mode. An RF tracking coil mounted in a medical device 190 is connected directly to a second pre-amplifier 156. As will be explained in more detail below, the medical device 190 is manipulated by the attending physician and NMR signals are detected by the tracking coil and processed to locate the position of the medical device. The amplified RF tracking coil signal is input to the transceiver module 150.

The NMR signals picked up by an RF coil is digitized by the transceiver module 150 and transferred to a memory module 160 in the system control 122. When an array of k-space image data has been acquired in the memory module 160, an array processor 161 operates to Fourier transform the k-space data into an array of image data which is presented to the attending physician on a display 134. This image data may also be conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

While a conventional MRI system may be used to implement the invention, in the preferred embodiment an MRI system which is designed to allow access by a physician is employed. Referring particularly to FIG. 1, when an intraoperative MR imaging procedure is conducted a patient is placed in the magnet system 103 and a region of interest in the patient is aligned near the system isocenter located between the two, spaced magnet rings 140 and 142. A physician standing between magnet rings 140 and 142 has unrestricted access to the region of interest in the patient.

The images to be produced by the MRI system are prescribed by selecting an appropriate NMR imaging pulse sequence to be executed by the pulse generator 121. The location and orientation of the slices or 3D region to be imaged is also prescribed and is determined by the particular patient anatomy the physician wants to see during the procedure being performed. This location and orientation remains fixed until new commands are applied to the pulse generator 121.

The present invention employs a tracking coil which is mounted in a medical device used by the physician. As will be described in more detail below, tracking coil measurement acquisitions are interleaved with the acquisition of image data and NMR tracking signals are detected by a tracking coil, are amplified by preamplifier 156 and coupled to transceiver module 150. These signals are then Fourier transformed by the array processor 161. The transformed NMR tracking data is used by the locator system 133 to produce an icon representing the medical device for display 134. The icon is overlaid on the NMR image of the patient anatomy at the location indicated by the tracking coil.

Figure 2:
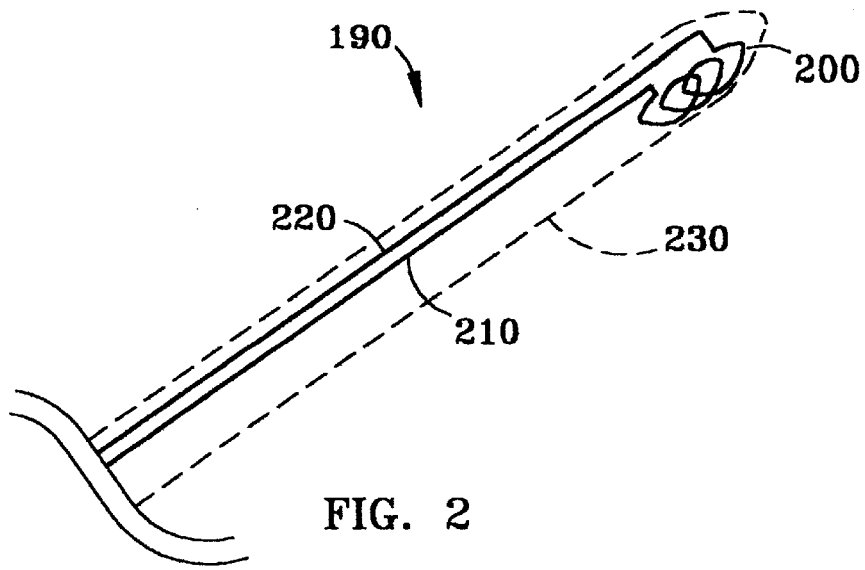
FIG. 2 is a schematic diagram of a tracking coil used to practice the preferred embodiment of the invention.

Referring particularly to FIG. 2, a medical device 190 designed for insertion into a patient includes a small RF tracking coil 200 mounted in its operative end. The medical device 190 may be, for example, a guide wire, a catheter, an endoscope, a laparoscope, a biopsy needle, an ablation device or other similar devices. Since the tracking coil 200 is small, its region of sensitivity is small and it only picks up NMR signals from excited spins in its immediate vicinity. These NMR signals are coupled to the T/R switch 154 in the MRI system by a pair of coaxial conductors 210 and 220. These conductors 210 and 220 are encased along with the tracking coil 200 in an outer shell 230 of the medical device 190.

Figure 3:
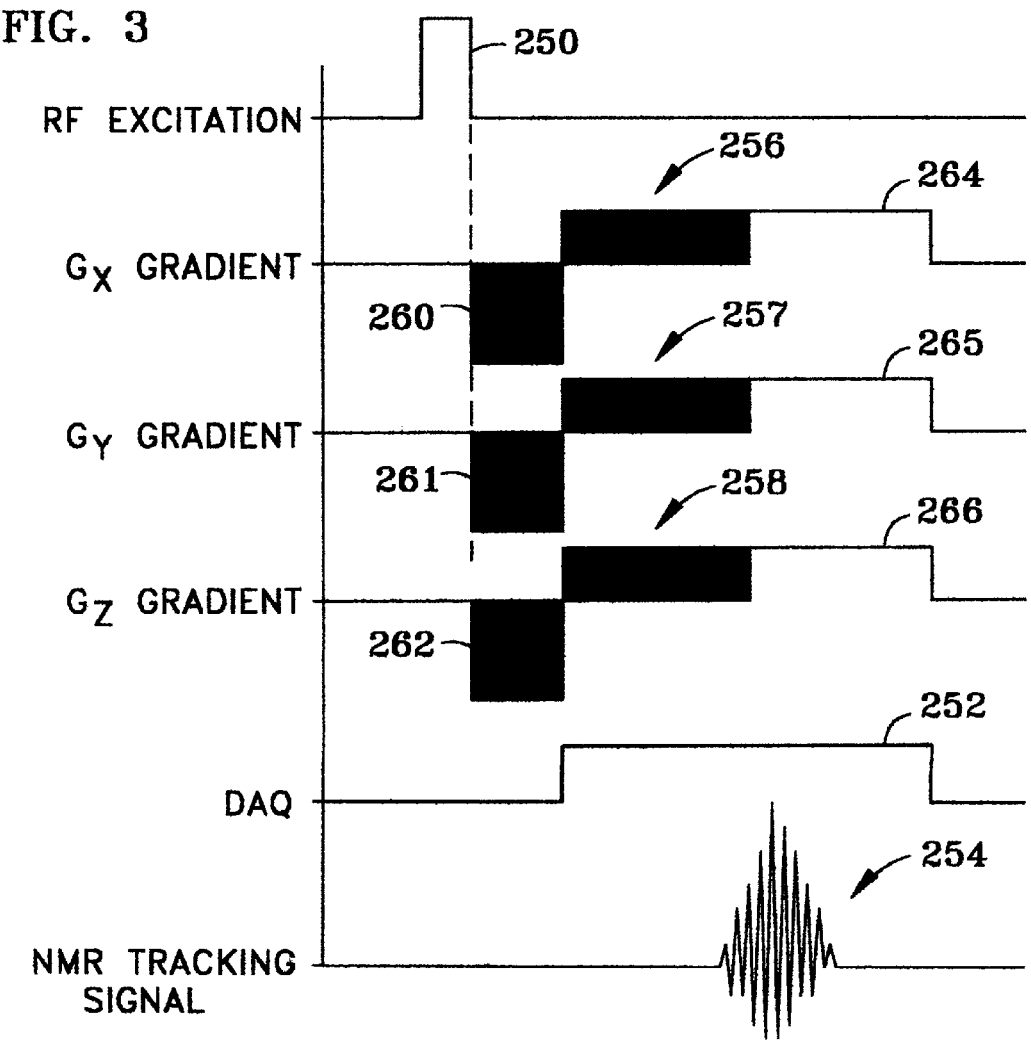
FIG. 3 is a graphic representation of an NMR pulse sequence used by the MRI system of FIG. 1 to measure the position of the tracking coil of FIG. 2.

The position of the tracking coil 200 relative to the gradient isocenter is measured using a position measurement NMR pulse sequence shown in FIG. 3. This gradient recalled echo pulse sequence yields a signal that is essentially a Fourier transform of a projection of the coil location along the readout gradient direction. Assuming that the tracking coil 200 is small, its position $S_1$ is modeled by:

$$S_1 = \frac{\Delta \omega}{\gamma G_1} \tag{1}$$

where $\Delta \omega$ is the measurement angular frequency of the gradient echo signal relative to $\omega_0$, the Larmor frequency $\gamma$, is the gyromagnetic ratio of the nuclear spins, and $G_1$ is the applied readout gradient. The three-dimensional position of each tracking coil 200 can be identified from three linearly independent gradient echoes.

As described in the above cited U.S. Pat. No. 5,353,795 issued on Oct. 11, 1994 and entitled "Tracking System To Monitor The Position Of A Device Using Multiplexed Magnetic Resonance Detection", which is incorporated herein by reference, errors arising from resonance offset conditions make it necessary to acquire more than three tracking coil measurements. While it is possible to acquire two measurements along each gradient axis to obtain the necessary error free tracking NMR data, such an approach requires six separate measurements. In the preferred embodiment a Hadamard MR tracking sequence is performed using the measurement pulse sequence of FIG. 3. It requires only four separate measurements to acquire a complete NMR tracking coil data set.

Referring particularly to FIG. 3, the tracking coil measurement pulse sequence includes a non-selective RF excitation pulse 250 which is applied to the MRI system whole body RF coil. It has a selected flip angle, typically chosen to be between 10 and 60 degrees and it produces transverse magnetization in spins located throughout the magnet bore. Three gradient waveforms 256, 257 and 258 are then applied to produce a gradient recalled NMR echo signal. The T/R switch 154 is controlled during a data acquisition window 252 to receive an NMR tracking signal 254 from the tracking coil 200. The three gradient waveforms 256, 257 and 258 are applied along the respective $G_x$, $G_y$ and $G_z$ gradient axes, and each includes a respective dephase lobe 260, 261 and 262 and a respective readout lobe 264, 265 and 266. As indicated by the cross hatching, the area of each dephasing lobe 260–262 is equal to one-half the area of the respective readout lobes 264–266.

In the measurement pulse sequence of FIG. 3, all of the gradients waveforms 256–258 all have the same polarity, which is designated herein as "+". "−" indicates the polarity of gradient pulses 260–262 having a polarity opposite that of waveforms 256–258. This pulse sequence is performed a total of four times with the polarity of the $G_x$, $G_y$ and $G_z$ gradient pulses selectively reversed as set forth in Table 1.

TABLE 1

|  | $G_x$ | $G_y$ | $G_z$ |
| --- | --- | --- | --- |
| acquisition 1 | − | − | − |
| acquisition 2 | + | + | − |
| acquisition 3 | + | − | + |
| acquisition 4 | − | + | + |

As indicated above, the four NMR tracking signals 254 are Fourier transformed to produce four corresponding projections $P_1$, $P_2$, $P_3$ and $P_4$. Together, these four projections form an NMR tracking data set from which the x, y and z coordinates of the tracking coil position can be calculated.

Figure 4:
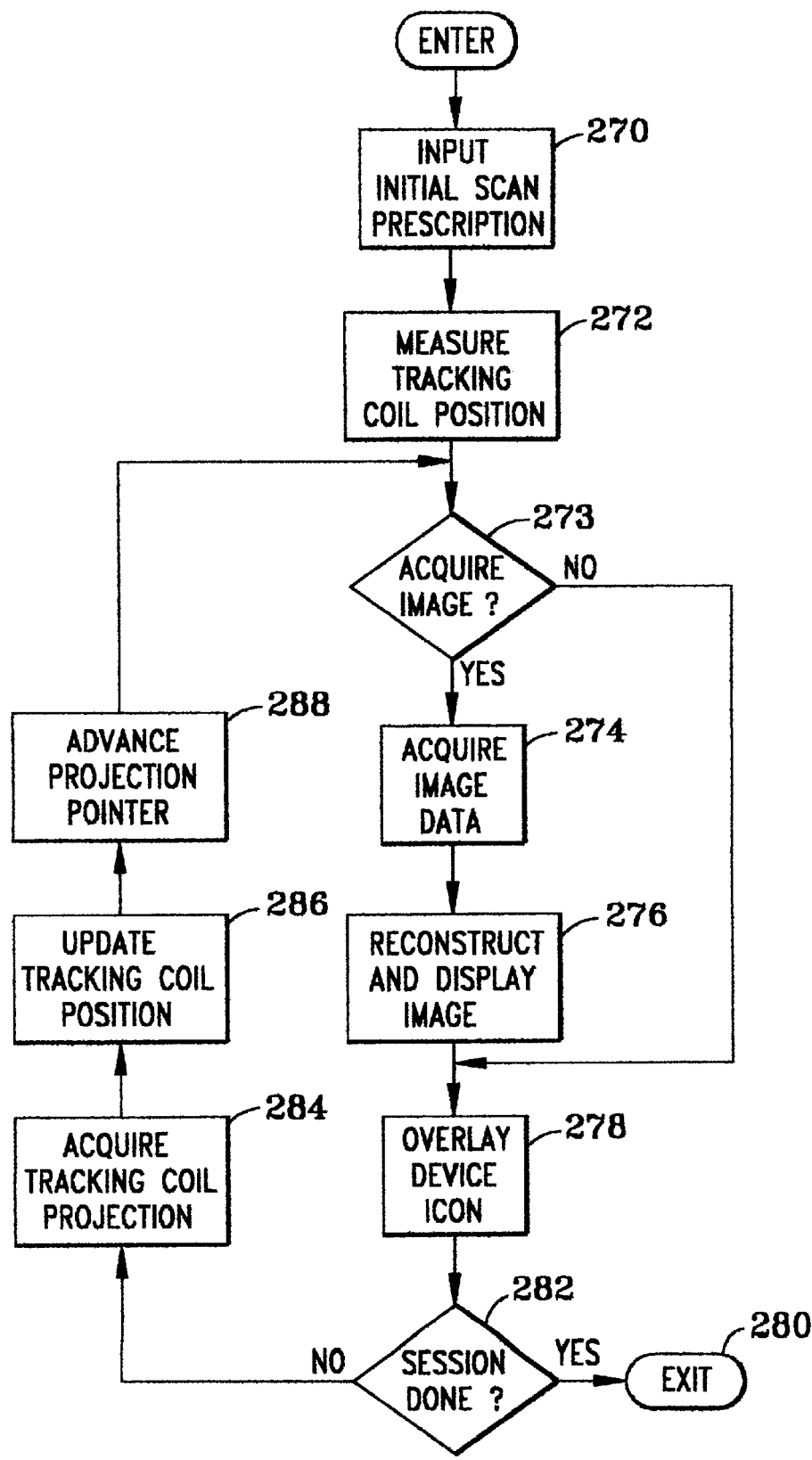
FIG. 4 is a flow chart of the preferred method used to practice the present invention.

The scan according to the preferred embodiment of the invention is carried out by a series of steps depicted in FIG. 4. When the procedure is started the operator enters the initial scan prescription as indicated at process block 270. As indicated above, this includes the selection of an appropriate NMR imaging pulse sequence and the scan parameters that locate and orient the slice plane or 3D volume which is to be imaged.

As indicated by process block 272, the next step is to measure the current position of the tracking coil 200. This is done by acquiring the four projections $P_1$–$P_4$ as described above with the Hadamard encoding indicated in Table 1. The locations of the signal peaks L1, L2, L3, L4 in each projection P1, P2, P3, P4 are then combined as follows:

$$S_x = -L_1 + L_2 + L_3 - L_4 \quad (1)$$

$$S_y = -L_1 + L_2 - L_3 + L_4 \quad (2)$$

$$S_z = -L_1 - L_2 + L_3 - L_4 \quad (3)$$

The x, y and z coordinates: Sx, Sy and Sz of the tracking coil 200 are determined from the results of equations (1), (2) and (3).

Referring still to FIG. 4, a loop is entered in which the device location is indicated on the display 134. As indicated at decision block 273, a determination is made first as to whether the anatomical image is to be updated. If so, image data is acquired using the prescribed imaging pulse sequence as indicated at process block 274. As indicated above, this acquired k-space image data is Fourier transformed to reconstruct an image of patient anatomy as indicated at process block 276, and this is output to the display 134 for immediate viewing by the attending physician. The locator system 133 also overlays a device icon on this image as indicated at process block 278 using the previously calculated tracking coil position to locate the icon on the display screen 134.

A number of variations are possible in the image acquisition and reconstruction steps 274 and 276. In come cases a complete k-space acquisition and image update may be performed, or in the alternative, only a partial k-space acquisition and image update may be performed as described, for example, in U.S. Pat. No. 4,830,012. Also, if there is little movement in the patient, or if movement occurs very slowly or only occasionally, it may not be necessary to acquire additional image data to update the anatomical image during each pass. This option is controlled by the physician who can slow or stop the rate of anatomic image updating. The location of the medical device icon will continue to be updated on the display 134 regardless of whether the anatomical image is updated.

If the scanning/tracking session is complete, the system exits at 280, otherwise, the system loops back at decision block 282. Before acquiring further image data at process block 274, however, the tracking coil measurement pulse sequence of FIG. 3 is performed once to acquire one of the four tracking coil projections $P_1$–$P_4$ as indicated at process block 284. Only one projection is acquired and a projection pointer is maintained that indicates which projection is to be acquired during each pass. The newly acquired projection is written over the corresponding outdated projection in the stored NMR tracking data set, and the tracking coil position is updated as indicated at process block 286 using equations (1), (2) and (3) with the newly acquired projection. As indicated at process block 288, the projection pointer is then advanced so that the next projection will be acquired during the next pass. This is done by incrementing the pointer by one until the fourth projection, $P_4$, is acquired and then resetting the pointer to the first projection, $P_1$. The projections $P_1$–$P_4$ are thus updated one at a time in round-robin order throughout the scan.

It should be noted that although the preferred embodiment described above employs Hadamard multiplexing of the MR tracking data, the round robin ordering and reconstruction of data can be advantageously applied to other data acquisition schemes.

If one considers an MR tracking protocol in which one projection of MR tracking data is acquired every 50 ms, and a four-step modulation scheme such as Hadamard multiplexing is performed, then using the prior art method, 4×50=200 ms would be required to compute each tracking point. This is a rate slower than human perception and some delay in the tracking display will be noted by the operator. By employing the present invention, the same MR tracking pulse sequence can be executed and data acquired every 50 ms. The initial tracking data would not be displayed until after the fourth acquisition, or a delay of 200 ms. Subsequent updates of the tracking position, however would be generated every 50 ms, resulting in an update rate of 20 tracking positions per second. This rate is four times faster than the prior art method and is at the threshold of human perception.

While several presently preferred embodiments of the novel high-speed tracking system have been described in detail herein, many modifications and variations will now become apparent to those skilled in the art. It is, therefore, to be understood that the appended claims are intended to cover all such modifications and variations as fall within the true spirit of the invention.

What is claimed is:

1. A method for tracking the location of a device within the field of view of an Magnetic Resonance Imaging (MRI) system, the steps comprising:
   a) attaching to the device a means for producing an nuclear magnetic resonance (NMR) tracking signal;
   b) acquiring; with the MRI system, an NMR tracking data set comprised of a plurality of NMR tracking signals, each tracking signal being acquired with a different tracking measurement pulse sequence;
   c) Fourier transforming the plurality of NMR tracking signals to produce a corresponding plurality of projections;
   d) calculating the location of the device using said plurality of projections;
   e) indicating the location of the device;
   f) re-acquiring, with the MRI system, one of the NMR tracking signals in the NMR tracking data set;
   g) Fourier transforming the re-acquired NMR tracking signal to produce a respective updated projection, said plurality of projections being updated with said respective updated projection;
   h) indicating an updated device location by repeating d) and e); and
   i) repeating f), g) and h) to provide a series of updated device location indications and in which all the NMR tracking signals in the NMR tracking data set are periodically re-acquired on a round-robin basis.

2. The method as recited in claim 1 which the device is a medical device and an image of anatomy is produced, and step e) is performed by displaying a device icon on the image.

3. The method as recited in claim 2 in which the image is produced from NMR image data acquired with the MRI system.

4. The method as recited in claim 3 in which the NMR image data is periodically re-acquired to produce an updated image and step f) is interleaved with the re-acquisition of NMR image data.

5. The method as recited in claim 1 in which the tracking pulse sequence directs the MRI system to:
   produce an RF excitation pulse that produces transverse magnetization in spins in the region of the device; and
   produce a readout gradient pulse which frequency encodes the acquired NMR tracking signals.

6. The method as recited in claim 5 in which said readout gradient pulse, is applied as three separate readout gradient pulses directed along three orthogonal gradient axes in the MRI system.

7. The method as recited in claim 6 in which the different tracking measurement pulse sequences are obtained by altering the polarity of one or more of the three separate readout gradient pulses.

8. The method as recited in claim 1 in which the means for producing an NMR tracking signal includes an RF coil mounted to the device (190), and the tracking measurement pulse sequence includes connecting the RF coil to the MRI system during a data acquisition window.

9. The method as recited in claim 8 in which the tracking measurement pulse sequence is a gradient recalled echo pulse sequence in which the MRI system is directed to produce a non-selective RF excitation pulse that produces transverse magnetization in spins surrounding the RF coil and produce a readout gradient pulse that produces a magnetic field gradient in a region surrounding the RF coil during the data acquisition window.

10. The method as recited in claim 9 in which an image is produced from NMR image data acquired with the MRI system and the device location is indicated in step e) on the image.

11. The method as recited in claim 10 in which tracking measurement pulse sequences are interleaved with image pulse sequences used to acquire the NMR image data.

12. A method for tracking the location of a device within the field of view of an Magnetic Resonance Imaging (MRI) system, the device being attached to a means for producing an MR tracking signal, the method comprising:
   a) acquiring, with the MRI system, a first Magnetic Resonance (MR) tracking data set comprised of a plurality of MR tracking signals, each tracking signal being acquired with a different tracking measurement pulse sequence;
   b) Fourier transforming each of the plurality of MR tracking signals to produce a respective plurality of projections;
   c) calculating the location of the device using said plurality of projections;
   d) indicating the location of the device;
   e) re-acquiring, with the MRI system, one of the MR tracking signals in the first MR tracking data set;
   f) Fourier transforming the re-acquired MR tracking signal to produce a respective updated projection; and,
   g) re-calculating and indicating an updated device location using the updated projection.

13. The method as recited in claim 12 further comprising
   h) re-acquiring a successive one of the MR tracking signals in said first MR tracking data set;
   i) Fourier transforming the re-acquired successive MR tracking signal to produce a respective updated projection;
   j) calculating and indicating an updated device location with the respective updated projection; and,
   k) repeating the re-acquisition, Fourier transformation, calculation and indication with MR tracking signals re-acquired successively to provide a series of updated device location indications.

* * * * *